United States Patent
Fuzzati

(10) Patent No.: US 11,696,887 B2
(45) Date of Patent: Jul. 11, 2023

(54) COSMETIC COMPOSITION COMPRISING A YEAST HYDROLYSATE

(71) Applicant: CHANEL PARFUMS BEAUTE, Neuilly sur Seine (FR)

(72) Inventor: Nicola Fuzzati, Neuilly sur Seine (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 17/592,101

(22) Filed: Feb. 3, 2022

(65) Prior Publication Data

US 2022/0257499 A1 Aug. 18, 2022

(30) Foreign Application Priority Data

Feb. 12, 2021 (EP) .................................. 21305186

(51) Int. Cl.
| | |
|---|---|
| *A61K 36/00* | (2006.01) |
| *A61K 8/9728* | (2017.01) |
| *A61K 8/9789* | (2017.01) |
| *A61Q 19/00* | (2006.01) |
| *A61Q 19/08* | (2006.01) |

(52) U.S. Cl.
CPC .......... *A61K 8/9728* (2017.08); *A61K 8/9789* (2017.08); *A61Q 19/007* (2013.01); *A61Q 19/08* (2013.01)

(58) Field of Classification Search
CPC ....... A61Q 19/007; A61Q 19/08; A61Q 19/00
See application file for complete search history.

(56) References Cited

U.S. PATENT DOCUMENTS

2013/0005007 A1 1/2013 Asano et al.

FOREIGN PATENT DOCUMENTS

| FR | 2927254 A1 | | 8/2009 |
|---|---|---|---|
| FR | 2976490 A1 | | 12/2012 |
| JP | 10174593 A | * | 6/1998 |
| JP | H10174593 A | | 6/1998 |
| JP | 2011182787 A | | 9/2011 |
| KR | 10-2016-0093427 A | | 8/2016 |
| KR | 10-2017-0126142 A | | 11/2017 |

OTHER PUBLICATIONS

Extended European Search dated Aug. 30, 2021, corresponding to European Application No. 21305186.5; 8 pages (with English Translation).

* cited by examiner

*Primary Examiner* — Qiuwen Mi
(74) *Attorney, Agent, or Firm* — Maier & Maier, PLLC

(57) ABSTRACT

A cosmetic composition including a yeast hydrolysate and to the use thereof in cosmetics, for promoting moisturization of the skin and/or protecting human skin against drying out and/or improving the barrier function and/or for an anti-ageing effect. The yeast hydrolysate is obtained by a process that includes solubilization of the yeast in water, enzymatic hydrolysis, separation of the soluble and insoluble phase and recovery of the soluble phase, enzymatic inactivation, and optionally concentration and sterilizing filtration.

9 Claims, No Drawings

COSMETIC COMPOSITION COMPRISING A YEAST HYDROLYSATE

FIELD

A subject of the present invention is a cosmetic composition comprising a hydrolysate of a yeast of the species *Pichia naganishii* obtained from an exudate of *Camellia japonica*, and also the use thereof in cosmetics, for promoting skin moisturization and/or protecting human skin against drying out and/or improving the barrier function and/or for preventing/reducing skin ageing.

BACKGROUND

The skin consists mainly of three layers, namely, starting from the most superficial layer, the epidermis, the dermis and the hypodermis.

The epidermis consists in particular of keratinocytes (in the majority), of melanocytes (involved in skin pigmentation) and of Langerhans cells. Its function is to protect the body from the outside environment and to ensure its integrity, and in particular to slow down the penetration of microorganisms or chemical substances, and to prevent evaporation of the water contained in the skin.

To do this, the keratinocytes undergo a continuous orientated maturation process over the course of which the keratinocytes located in the basal layer of the epidermis form, at the terminal stage of their differentiation, corneocytes which are totally keratinized dead cells in the form of cornified envelopes consisting of proteins and lipids such as ceramides. During this differentiation process, intercorneocyte epidermal lipids are also formed and then organized in the form of bilayers (sheets) in the stratum corneum. They participate, with the abovementioned cornified envelopes, in the barrier function of the epidermis.

The barrier function of the epidermis can however be disrupted under certain climatic conditions (under the effect of cold and/or wind, for example), or else under the effect of stress or fatigue, in particular, thus promoting the penetration of allergens, of irritant agents or of microorganisms which thus bring about drying out of the skin capable of generating feelings of discomfort such as tautness or redness, and also of detrimentally modifying the radiance of the complexion and the suppleness of the skin.

In order to prevent this phenomenon or to correct it, it is known practice to apply to the skin cosmetic compositions containing hygroscopic agents, such as sugars or polyols, intended to capture the water present in the skin and thus slow down its evaporation. Moreover, these compositions frequently incorporate active agents which act on one or more of the various biological targets involved either in skin regeneration processes, in particular in keratinocyte differentiation, epidermal lipid synthesis and corneocyte cohesion, or in the endogenous synthesis of constituents of the natural moisturizing factor (NMF) of the skin, in particular in the synthesis of proteoglycans.

Proteoglycans play, moreover, an important role in maintaining moisturization and in firming of the skin, and most particularly hyaluronic acid. However, with age, the hyaluronic acid decreases in amount and in quality, leading to dryness and a slackening of the skin, and the loss of its elasticity, which thus leads to the appearance of wrinkles. It is therefore necessary to find active agents capable of stimulating the production of hyaluronic acid.

Examples of such active agents are in particular α- and β-hydroxy acids, in particular lactic acid, glycolic acid and salicylic acid, urea, or aminosulfonic compounds.

However, there is still the need to provide new cosmetic active agents which allow a more efficient skin moisturization and anti-ageing prevention.

In addition, given the ever increasing search by consumers for natural products containing as few synthetic ingredients as possible, and the increasingly onerous regulatory constraints that weigh on compounds from the chemical industry, it would be desirable for these cosmetic active agents to be of natural origin.

SUMMARY

This is the objective of the present invention which, to this effect, provides a new cosmetic composition comprising a hydrolysate of a yeast of the species *Pichia naganishii*.

The yeast *Pichia naganishii*, also known as *Ogataea naganishii*, can be isolated from an exudate of Japanese camelia or *Camellia japonica*. This specific yeast has up until now been identified only on two plants, *Camellia japonica* and *Sakaki ochnacea* and in a single geographical region located in Japan. A strain of the yeast *Pichia naganishii* can also be obtained from the ATCC (American Type Culture Collection) bank under number 32418.

Patents relating to the production of molecules by the yeast *Pichia naganishii*, such as glycolic acid, chloropropanediol derivative, hydroxy keto ester, propanol, muscone and glycolate, are known from the prior art, but no prior art document describes a cosmetic use or an active ingredient derived from this yeast.

Surprisingly, the inventors have demonstrated that the application of *Pichia naganishii* hydrolysates to keratinocyte cultures makes it possible to stimulate the production of hyaluronic acid, and also the synthesis of several proteins involved in the barrier function and moisturization of the skin. These hydrolysates can thus be used for preventing/slowing down skin ageing and also for improving the moisturization and the barrier function of the skin.

The invention, according to a first aspect, therefore relates to a composition comprising a hydrolysate of the biomass of the yeast *Pichia naganishii*. In particular, the invention relates to a composition comprising at least one hydrolysate of a yeast of the species *Pichia naganishii*, said yeast being obtained from an exudate of *Camellia japonica*.

The invention also relates to a composition comprising at least one hydrolysate of a yeast of the species *Pichia naganishii* obtained according to the preparation process comprising in particular solubilization of the yeast *Pichia naganishii* in water, enzymatic hydrolysis, separation of the soluble and insoluble phase and recovery of the soluble phase, enzymatic inactivation, and optionally concentration of the hydrolysate followed by sterilizing filtration.

The *Pichia naganishii* hydrolysate is of natural origin and advantageously has a moisturizing and barrier function effect without attacking it and also an anti-ageing effect. It thus satisfies the problems of the prior art. It can be used for cosmetic applications, preferentially in a form suitable for topical application. The cosmetic composition comprises at least 0.1% by weight of the *Pichia naganishii* hydrolysate.

According to a second aspect, the invention relates to a non-therapeutic cosmetic use of a *Pichia naganishii* hydrolysate or of the composition containing same, for improving moisturization and/or protecting human skin against drying out and/or improving the barrier function and/or for preventing/reducing skin ageing.

Other characteristics and advantages will emerge from the detailed description of the invention and from the examples which follow.

DETAILED DESCRIPTION

Definitions

The term "*Pichia naganishii* hydrolysate" is intended to mean any active ingredient derived from the yeast *Pichia naganishii*. This hydrolysate is the product obtained by means of a process comprising at least one step of hydrolysis of *Pichia naganishii*. The term "*Pichia naganishii* hydrolysate" excludes the molecules produced solely by fermentation of *Pichia naganishii*.

The term "*Pichia naganishii*" is intended to mean any yeast of the family Saccharomycetaceae, of the genus *Pichia* and of the species *Pichia naganishii*. A strain of the yeast *Pichia naganishii* has been registered in a yeast collection, under number ATCC 32418. It is also known under the name: *Ogataea naganishii*. *Pichia naganishii* can be isolated from an exudate of *Camellia japonica*.

An "exudate of *Camellia japonica*" is a substance excreted by the *Camellia japonica* plant.

*Pichia naganishii* Hydrolysate

A subject of the present invention is thus a cosmetic composition comprising at least one hydrolysate of a yeast of the species *Pichia naganishii*.

According to one preferred embodiment, the yeast *Pichia naganishii* can be obtained from an exudate of *Camellia japonica* or from the strain deposited under number ATCC 32418. The hydrolysate can in particular comprise proteins and/or carbohydrates. When the hydrolysate comprises proteins, it preferentially comprises between 20% and 60% of proteins, by weight of dry matter of the hydrolysate.

According to one embodiment, the hydrolysate comprises between 5% and 25% of carbohydrates, more preferentially 12% by weight of dry matter of the hydrolysate.

Preferentially, the ash content is between 5% and 35% by weight, even more preferentially between 20% and 30%.

The raw ash content can be determined by weighing the residues derived from the incineration of the samples of the hydrolysate at 550° C. in an electric muffle furnace.

The hydrolysate is preferentially obtained by enzymatic hydrolysis. Thus, the hydrolysate is preferentially an enzymatic hydrolysate. By way of example, the enzymes used for the hydrolysis can be a protease or a carbohydrate.

The *Pichia naganishii* hydrolysate can be in solid form or in liquid form.

When it is in liquid form, the hydrolysate is in the form of a clear liquid, pale yellow in colour, with a characteristic odour.

When it is in solid form, the hydrolysate is linked to a support chosen from maltodextrin, gum arabic, soybean lecithin or isomalt. According to one particularly suitable embodiment, the hydrolysate+support combination consists of at least 10% by weight of hydrolysate and at most 90% by weight of support.

In the case of a solid form in which the hydrolysate is linked to a support, the protein, sugar and ash contents stated above are modified, the support generally consisting predominantly of sugars.

The *Pichia naganishii* hydrolysate can optionally be integrated into a cosmetic composition, in particular a composition comprising at least 0.1% by weight of said hydrolysate. In particular, the composition is in a form suitable for topical application, such as a cream or a lotion.

Extraction Process

The *Pichia naganishii* hydrolysate can be obtained by any process comprising at least one step of hydrolysis of *Pichia naganishii*. Particularly preferably, it is obtained by means of a process comprising an enzymatic hydrolysis step.

Prior to the process for obtaining the hydrolysate as such, it is advisable to produce the *Pichia naganishii* biomass. This step is carried out according to the method of culture of the yeasts in a medium suitable for their development, in a manner conventional for those skilled in the art. Once the biomass has been obtained, a hydrolysis is carried out for the purpose of obtaining active molecules.

According to one particularly suitable embodiment, the *Pichia naganishii* hydrolysate is obtained by carrying out the following steps:
  solubilization in a proportion of at least 40 g/L of the yeast *Pichia naganishii* in water,
  hydrolysis, preferentially enzymatic hydrolysis,
  separation of the soluble and insoluble phase and recovery of the soluble phase,
  enzymatic inactivation, and optionally filtration,
  optionally concentration and sterilizing filtration.

The hydrolysis conditions are chosen for hydrolyzing both the yeast walls and the yeast intracellular medium; preferentially, the hydrolysis is carried out enzymatically.

The separation of the soluble and insoluble phases is carried out by any means, for example by centrifugation, filtration or decanting. Preferentially, the separation of the soluble and insoluble phases is carried out by centrifugation, thus allowing the recovery of the soluble phase containing, inter alia, the soluble proteins.

The inactivation of the enzyme is preferentially carried out by heat treatment. This inactivation is then carried out according to the enzyme supplier's recommendations.

Optionally, the process comprises a filtration step after the recovery of the soluble phase in order to remove the particles still in suspension. Thus, this filtration step allows the purification of the recovered soluble phase and is carried out in order to remove the high-molecular-weight molecules (enzymes and polymers, etc.).

The hydrolysate obtained at this stage can optionally be further concentrated and/or purified, preferentially by means of successive steps of ultrafiltrations through filters with different porosities, while preserving the filtrates at each step, and/or by a chromatographic method.

The hydrolysate obtained after hydrolysis and filtration, before or after concentration and sterilizing filtration, is a *Pichia naganishii* hydrolysate in liquid form.

The hydrolysate obtained can then be dried and linked to a support, so as to be in solid form. This phase can be performed by carrying out the following steps:
  a spray-drying support, preferably maltodextrin, is added to the *Pichia naganishii* hydrolysate, up to 90% (by mass/volume);
  this solution is then concentrated under vacuum;
  the bacteria possibly present are removed by heat treatment;
  the spray drying makes it possible to obtain a powder.

The steps of the processes described above, taken individually, are routine in the field of extractions of active agents from natural raw materials and those skilled in the art are able to adjust the reaction parameters thereof on the basis of their general knowledge.

Cosmetic Composition

A subject of the present invention is a cosmetic composition comprising, in a physiologically acceptable medium, at least one *Pichia naganishii* hydrolysate.

The composition used according to the invention generally comprises, in addition to the hydrolysate described above, a medium which is physiologically acceptable and preferably cosmetically acceptable, that is to say which is suitable for use in contact with human skin without a risk of toxicity, of incompatibility, of instability, and of allergic response, and in particular which does not cause feelings of discomfort (redness, tautness, stinging).

It can be advantageously applied to the skin of the face, the neck, the hands and optionally the neckline or, as a variant, to any part of the body. The composition containing this hydrolysate can be applied in the morning and/or in the evening, to the entire face, neck, hands and optionally neckline, or even body.

Advantageously, said cosmetic or dermatological composition can be in the form of a powder, an emulsion, a microemulsion, a nanoemulsion, a suspension, a solution, a lotion, a cream, an aqueous or aqueous-alcoholic gel, a foam, a serum, an aerosol solution or dispersion, or a dispersion of lipid vesicles.

In the case of an emulsion, it may be a water-in-oil or oil-in-water emulsion.

The cosmetic or dermatological composition according to the invention may also comprise a solvent chosen according to the various ingredients and the form of the administration. By way of examples, mention may be made of water (preferably demineralized water or floral waters), or an alcohol such as ethanol.

Said cosmetic composition may also comprise, in addition to the *Pichia naganishii* hydrolysate:
- at least one additive that is normal in the field, such as for example at least one compound chosen from an emollient or humectant, a gelling agent and/or thickener, a surfactant, an oil, an active agent, a dye, a preservative, an antioxidant, an organic or inorganic powder, a sunscreen and a fragrance;
- one or more humectant(s), such as polyols (glycerol, diglycerol, propanediol, caprylyl glycol, pentylene glycol, hexanediol), sugars, glycosaminoglycans such as hyaluronic acid and salts and esters thereof; and polyquaterniums such as Lipidure PMB. Said humectant will be present in the composition in a content of about from 0% to 30%, preferably 0.005% to 10% by total weight of the composition.
- One or more emollient(s) which can be chosen for example from esters such as jojoba esters, fatty acid esters and fatty alcohol esters (octyldodecyl myristate, triethylhexanoin, dicaprylyl carbonate, isostearyl isostearate, caprylic/capric triglyceride), butters such as shea butter (Butyrospernum parkii butter extract, shea butter ethyl esters, sold under the names Lipex Sheasoft, Lipex Shea-U, Lipex Shea, Lipex Shealight, Lipex Shea Tris) or moringa butter (moringa oil/hydrogenated moringa oil esters), waxes (Acacia decurrens flower wax & Helianthus annuus cera seed wax, C10-18 triglycerides), plant oils, phytosqualane, alkanes (undecane, tridecane). Said emollient will be present in the composition in a content of about from 0.1% to 30%, preferably 0.5% to 10% by total weight of the composition.
- One or more aqueous-phase gelling agent(s) and/or thickener(s), chosen for example from cellulose-based derivatives, gums of plant origin (guar, locust bean, alginates, carrageenans, pectins), of microbial origin (xanthan), clays (laponite), hydrophilic or amphiphilic, crosslinked or non-crosslinked homo- and copolymers of acryloylmethylpropanesulfonic acid (AMPS) and/or of acrylamide and/or of acrylic acid and/or of salts or esters of acrylic acid (sold under the names Aristoflex AVC, Aristoflex AVS, Aristoflex HMB, Simulgel NS, Simulgel EG, Simulgel 600, Simulgel 800, Pemulen, carbopol, Sepiplus 400, Seppimax zen, Sepiplus S, Cosmedia SP). Said gelling agent and/or thickener will be present in the composition in a content of about from 0.1% to 10% by total weight of the composition.
- One or more surfactant(s), such as lecithins, polyglycerol derivatives, sugar derivatives (glucoside derivatives or xyloside derivatives sold under the name Montanov 68, Montanov 202, Montanov 82, Montanov L, Easynov), or phosphates (C20-22 alkyl phosphate sold under the name Sensanov WR). Said surfactant will be present in a content of about from 0.1% to 8%, preferably from 0.5% to 3% by weight, relative to the total weight of the composition.
- One or more active agent(s) of a natural, biotechnological or synthetic origin having a biological activity and having an efficacy on the skin via biological sites, for example chosen from vitamins such as vitamin C and derivatives thereof (ascorbyl glucoside, 3-O-ethyl ascorbic acid, ascorbyl tetraisopalmitate), vitamin A and derivatives thereof, vitamin E and derivatives thereof, vitamin B3 or niacinamide, panthenol, trace elements, allantoin, adenosine, peptides (palmitoyl tetrapeptide-7, palmitoyl tripeptide-1, palmitoyl pentapeptide-4, acetyl dipeptide-1 cetyl ester, acetyl tetrapeptide-5, sold under the name NP Rigin, Matrixyl 3000, Idealift, Eyeseryl), plant extracts (Glycyrrhiza glabra extract, Centella asiatica leaf extract, Secale cereale seed extract), yeast extracts, alpha-hydroxy acids such as glycolic acid or lactic acid, tranexamic acid and derivatives thereof such as tranexamic acid cetyl ester, etc. Said active agent will be present in the composition in a content of about from 0.1% to 10% by total weight of the composition.

Other additives normally used in cosmetics may also be present in the composition according to the invention, in particular preservatives, antioxidants or fragrances well known in the technical field.

Those skilled in the art are capable of choosing, among all these optional additives, both the nature and the amount of those that will be added to the composition, in such a way that said composition retains all of its properties.

Cosmetic Use

The cosmetic composition according to the invention comprises a *Pichia naganishii* hydrolysate that is particularly efficacious for moisturizing the skin and reinforcing the barrier function. In particular, when applied to the skin it makes it possible to:
maintain moisturization,
reinforce the barrier function,
protect human skin against drying out,
reinforce the biomechanical properties of the skin,
reduce the appearance of wrinkles.

Advantageously, the cosmetic composition according to the invention comprises a *Pichia naganishii* hydrolysate capable of stimulating hyaluronic acid synthesis in human keratinocytes and thus promoting a moisturizing and anti-ageing action.

The cosmetic composition according to the invention comprises a *Pichia naganishii* hydrolysate which also makes it possible to increase the expression of hyaluronan synthase 2, of aquaporin 3, of caspase 14, of filaggrin, of desmoglein- 1, of loricrin, in order to improve the moisturization of the skin whilst maintaining the homeostasis of the barrier function.

The invention thus targets a non-therapeutic cosmetic use of a *Pichia naganishii* hydrolysate for its cosmetic effects, alone or in a composition, in particular for at least one cosmetic effect chosen from the improvement of skin moisturization, reinforcement of the skin barrier and prevention/reduction of skin ageing.

For the purposes of the invention, the term "non-therapeutic use" is intended to mean a cosmetic use of the *Pichia naganishii* hydrolysate or of a composition comprising same, intended for healthy subjects who are not ill, in particular for subjects with healthy skin.

The invention is presently illustrated by the following nonlimiting examples.

EXAMPLES

Example 1—Active Ingredient (AI1)

The *Pichia naganishii* hydrolysate of Example 1 (AI1) is obtained by means of the following process:
  solubilization of *P. naganishii* in water, preferentially in a proportion of 50 g/l,
  enzymatic hydrolysis with a carbohydrase,
  separation of the soluble and insoluble phases,
  enzymatic inactivation by heat treatment,
  filtration,
  concentration,
  filtration and sterilizing filtration.

The *Pichia naganishii* hydrolysate obtained has the following characteristics: 45% of carbohydrates and 7% of proteins (as percentage relative to the dry matter).

Example 2—Active Ingredient (AI2)

The *Pichia naganishii* hydrolysate of Example 2 (AI2) is obtained by means of the following process:
  solubilization of *P. naganishii* in water, preferentially in a proportion of 50 g/l,
  enzymatic hydrolysis with a protease,
  separation of the soluble and insoluble phases,
  enzymatic inactivation by heat treatment,
  filtration,
  concentration,
  filtration and sterilizing filtration.

The *Pichia naganishii* hydrolysate obtained has the following characteristics: 12% of carbohydrates and 29% of ash and 59% of proteins (as percentage relative to the dry matter). The hydrolysate is in the form of a clear liquid aqueous solution which is pale yellow in colour with a characteristic odour.

Example 3—Active Ingredient (AI3)

The *Pichia naganishii* hydrolysate of Example 3 (AI3) is obtained by means of a process similar to that of Example 2 and comprises a filtration step using carbon.

The *Pichia naganishii* hydrolysate obtained has the following characteristics: 45% of carbohydrates and 11% of proteins (as percentage relative to dry matter).

Example 4—Active Ingredient Outside the Invention (AI4)

The hydrolysate of Example 4 (AI4) is obtained by means of the following process:
  solubilization of *Pichia anomala* in water, preferentially in a proportion of 20 g/l,
  basic hydrolysis of the *Pichia anomala* solution,
  separation of the soluble and insoluble phases, for example by filtration, centrifugation or decanting,
  recovery of the soluble phase,
  filtration and purification in order to recover the molecules,
  enzymatic hydrolysis of the proteins, preferentially by means of a protease,
  filtration and purification in order to recover the biopeptides of size smaller than 5000 Da.

Example 5—Effect of the *Pichia naganishii* Hydrolysate on Hyaluronic Acid Synthesis The objective of this test is to compare the effect of the *Pichia naganishii* hydrolysate (AI2) in vitro on human keratinocytes, on hyaluronic acid synthesis, with the effect of an active ingredient outside the invention (AI4).

The procedure of the study is described below.

Normal human keratinocytes are seeded and then incubated at 37° C. in an incubator containing 5% $CO_2$. The culture medium is then removed and replaced with medium containing the active ingredients:
  AI2 at 1.00% (V/V)
  AI4 at 1.00% (V/V).

The cells are then incubated at 37° C. in an atmosphere containing 5% $CO_2$ for 48 hours. The supernatants are recovered before being analyzed by ELISA assay.

The results are presented in Table 1 below.

TABLE 1

| | Hyaluronic acid synthesis (%) | Amount of hyaluronic acid/ control (%) |
|---|---|---|
| Control | 100 | |
| AI2 1.00% | 150 | +50 |
| AI4 1.00% | 80 | − |

Thus, only the *Pichia naganishii* hydrolysate (AI2) stimulates hyaluronic acid synthesis.

The study is also carried out at various doses of active ingredients (hydrolysates) as follows:
  AI1 at 0.25% and 1.00% (V/V)
  AI2 at 0.25% and 1.00% (V/V)
  AI3 at 0.25% and 1.00% (V/V)

The results are presented in Table 2 below.

TABLE 2

| | Hyaluronic acid synthesis (pg/µg proteins) | Amount of hyaluronic acid/ Control (%) |
|---|---|---|
| Control | 399 ± 64 | |
| AI1 0.25% | 527 ± 141 | +32 |
| AI1 1.00% | 628 ± 94 | +57 |
| AI2 0.25% | 559 ± 113 | +40 |
| AI2 1.00% | 598 ± 90 | +50 |
| AI3 0.25% | 541 ± 100 | +36 |
| AI3 1.00% | 591 ± 84 | +48 |

Thus, the *Pichia naganishii* hydrolysates at 1% stimulate hyaluronic acid synthesis by 57% for AI1, 50% for AI2, 48% for AI3. As explained above, hyaluronic acid plays an important role in maintaining the moisturization and in the elasticity of the skin. The decrease in hyaluronic acid content with age leads to a drying out and a slackening of the skin, and also a loss of its elasticity, thus leading to the appearance of wrinkles. As is known by those skilled in the art, products which stimulate hyaluronic acid synthesis in the skin make it possible to prevent the skin from drying out, to improve its moisturization and to reduce/prevent its ageing (and in particular the appearance of wrinkles). The *Pichia naganishii* hydrolysates can thus be used for these applications.

Example 6—Effect of the *Pichia naganishii* Hydrolysate on the Expression of HAS-2 and Aquaporin 3

The objective of this study is to evaluate the effect of the *Pichia naganishii* hydrolysates AI1, AI2 and AI3 regarding their ability to increase the expression of mRNAs encoding HAS-2 and aquaporin 3. This study was carried out on normal human keratinocytes by quantitative PCR.
The procedure of the study is described below.
Normal human keratinocytes are seeded and then incubated at 37° C. in an incubator containing 5% $CO_2$.
The culture medium is then removed and replaced with medium containing the active ingredients derived from *Pichia naganishii*:
  AI1 at 0.25% and 1.00% (V/V)
  AI2 at 0.25% and 1.00% (V/V)
  AI3 at 0.25% and 1.00% (V/V).
The cells are then incubated at 37° C. in an atmosphere containing 5% $CO_2$. The cells are recovered and the total RNAs are extracted for the study of HAS-2, of aquaporin 3, caspase 14 and filaggrin. The RNAs were reverse-transcribed and the complementary DNAs obtained were analyzed by using the quantitative PCR technique.
The mRNAs of reference controls were also analyzed in parallel to the mRNAs of aquaporin 3 and HAS-2.
The quantification of the incorporation of fluorescence (SYBR Green) is measured continuously using a thermocycler. The Ct analysis (relative quantification) is carried out using software. The results are presented in Table 5 below.

TABLE 5

| | Expression/Control (%) | |
|---|---|---|
| | HAS-2 | aquaporin 3 |
| AI1 0.25% | +20 | +14 |
| AI1 1.00% | +4 | +43 |
| AI2 0.25% | +50 | +46 |
| AI2 1.00% | +36 | +130 |
| AI3 0.25% | +12 | +9 |
| AI3 1.00% | +18 | +95 |

Thus, the *Pichia naganishii* hydrolysates AI1, AI2 and AI3 increase the expression of HAS-2 and of aquaporin 3, which are proteins known for their moisturizing action. These hydrolysates can thus be used in order to improve skin moisturization.

Example 7—Effect of the *Pichia naganishii* Hydrolysate on the Genes of the Epidermal Physical Barrier The study aims to evaluate the effect of the *Pichia naganishii* hydrolysate AI2 with regard to its capacity to increase the expression of the genes of the epidermal physical barrier: desmoglein-1, filaggrin, loricrin, caspase 14.
This study was carried out on normal human keratinocytes by quantitative PCR.
The procedure of the study is described below.
Normal human keratinocytes are seeded and then incubated at 37° C. in an incubator containing 5% $CO_2$. The culture medium is then removed and replaced with medium containing the product derived from AI2 at 0.5%, 1.0% and 2.0% (V/V).
The cells are then incubated at 37° C. in an atmosphere containing 5% $CO_2$. The total RNAs extracted were reverse-transcribed and the complementary DNAs obtained were analyzed using the quantitative PCR technique.
The mRNAs of the genes: desmoglein-1, filaggrin, loricrin, caspase 14 were analyzed in parallel to the mRNAs of reference controls for standardization.
The fluorescence (SYBR Green) is measured continuously by means of a thermocycler. The Ct analysis (relative quantification) is carried out using software.
The results are presented in Table 6 below.

TABLE 6

| | Expression/Control (%) | | |
|---|---|---|---|
| | AI2 0.5% | AI2 1.0% | AI2 2.0% |
| Desmoglein-1 | 80 | 84 | 184 |
| Filaggrin | 33 | Va | 64 |
| Loricrin | 91 | Va | 89 |
| Caspase 14 | 95 | 150 | 370 |

Va = aberrant values

Tested at 2.0%, the *Pichia naganishii* hydrolysate AI2 significantly increases the expression of the genes of the epidermal physical barrier. It thus makes it possible to reinforce the barrier function of the skin.

Example 8—Effect of the *Pichia naganishii* Hydrolysate on the Membrane Network, in Particular on the Tight Junctions The aim of this study is to visualize the effect of the *Pichia naganishii* hydrolysates on the membrane network formed by zonula occludens ZO-1, one of the major constituents of tight junctions.
The study was carried out by immunocytology on normal human keratinocytes after attack with sodium lauryl sulfate (SLS) at 0.4 mM.
The procedure of the study is described below.
Normal human keratinocytes are seeded and then incubated at 37° C. in an incubator containing 5% $CO_2$. The normal human keratinocytes are then treated with a 1 mM $CaCl_2$ solution for 48h in order to allow the formation of the tight junction network. The normal human keratinocytes are then treated with a 0.4 mM SLS solution for 30 minutes.
At the end of the incubation, the SLS solution is removed and replaced with medium containing the *Pichia naganishii* hydrolysates:
  AI1 at 0.25% and 1.00% (V/V)
  AI2 at 0.25% and 1.00% (V/V)
  AI3 at 0.25% and 1.00% (V/V).
The cells are incubated for 48h in an incubator at 37° C. in a humid atmosphere containing 5% $CO_2$.
The cells are immunolabelled by means of a fluorophore. Visualization is carried out under a microscope coupled to an image analysis system. The intensity of the ZO-1 labelling is proportional to the intensity of green fluorescence present at the cell membrane. The stronger the green colour, the higher the amount of ZO-1 synthesis.

Furthermore, a quantitative image analysis was carried out using the Matlab software. This quantification is expressed in arbitrary units (AU).

The results are the following. After SLS attack on human keratinocytes, the ZO-1 membrane network induced by $CaCl_2$ is greatly impaired.

Tested at 0.25% then at 1% on human keratinocytes having undergone attack, the *Pichia naganishii* hydrolysates increase respectively the synthesis and the formation of the ZO-1 membrane network by:

127% and 139% for AI1
33% and 46% for AI2
47% and 79% for AI3.

Thus, the *Pichia naganishii* hydrolysates increase the expression of the genes involved in tight junction formation, thus making it possible to improve the barrier function and the moisturization of the skin.

Example 9—Cosmetic Composition

The following compositions can be prepared in a manner conventional for those skilled in the art. The amounts indicated below are expressed as weight percentages. The ingredients in capital letters are identified in accordance with the INCI name.

| A-oil/water emulsion gel | |
|---|---|
| INCI name | (% W/W) |
| *LIMNANTHES ALBA* (MEADOWFOAM) SEED OIL | 1-10 |
| *BUTYROSPERMUM PARKII* BUTTER (LIPEX SHEASOFT) | 1-10 |
| *BUTYROSPERNUM PARKII* BUTTER EXTRACT (*LIPEX SHEA TRIS*) | 1-10 |
| *CAMELLIA OLEIFERA* SEED OIL | 1-10 |
| CAPRYLIC/CAPRIC TRIGLYCERIDE | 1-10 |
| SQUALANE | 1-10 |
| AMMONIUM ACRYLOYLDIMETHYLTAURATE/ VP COPOLYMER | 0.1-5 |
| ACRYLATES/C10-30 ALKYL ACRYLATE CROSSPOLYMER | 0.1-2 |
| XANTHAN GUM | 0.01-5 |
| *TREMELLA FUCIFORMIS* (MUSHROOM) EXTRACT | 0.01-5 |
| *ORYZA SATIVA* (RICE) POWDER | 0.1-5 |
| SODIUM HYALURONATE | 0.01-3 |
| GLYCERIN | 1-30 |
| POLYQUATERNIUM-51 | 1-10 |
| TOCOPHERYL ACETATE | 0.1-5 |
| NIACINAMIDE | 0.1-5 |
| *SPHINGOMONAS* FERMENT EXTRACT | 0.01-5 |
| *POLIANTHES TUBEROSA* | 0.01-5 |
| BETAINE | 0.1-10 |
| SODIUM PCA | 0.5-5 |
| SACCHARIDE ISOMERATE | 0.5-5 |
| *PICHIA NAGANISHII* HYDROLYSATE | 0.001-10 |
| YEAST EXTRACT | 0.1-5 |
| GLYCOLS (CAPRYLYL GLYCOL AND/OR PENTYLENE GLYCOL AND/OR BUTYLENE GLYCOL AND/OR PROPANEDIOL) | 0.1-10 |
| WATER | Qs 100 |

| b-oil/water emulsion cream | |
|---|---|
| INCI name | (% w/w) |
| JOJOBA ESTERS | 1-5 |
| *LIMNANTHES ALBA* (MEADOWFOAM) SEED OIL | 0.1-5 |
| CANOLA OIL | 1-10 |
| *ARGANIA SPINOSA* KERNEL OIL | 0.1-10 |
| *MORINGA* OIL/HYDROGENATED | 1-10 |
| *MORINGA* OIL ESTERS | |
| C8-12 ACID TRIGLYCERIDE | 1-5 |
| LAUROYL LYSINE | 1-5 |
| *CAMELLIA OLEIFERA* SEED OIL | 1-10 |
| PHYTOSTERYL/OCTYLDODECYL LAUROYL GLUTAMATE | 1-5 |
| SQUALANE | 1-10 |
| AMMONIUM ACRYLOYLDIMETHYLTAURATE/ VP COPOLYMER | 1-5 |
| CETEARYL ALCOHOL & CETEARYL GLUCOSIDE | 1-7 |
| HYDROGENATED LECITHIN | 0.1-5 |
| *CHONDRUS CRISPUS* (CARRAGEENAN) | 0.1-5 |
| SCLEROTIUM GUM | 0.01-2 |
| *CENTELLA ASIATICA* LEAF EXTRACT | 0.1-5 |
| ADENOSINE | 0.1-0.5 |
| NIACINAMIDE | 0.1-5 |
| *SECALE CEREALE* (RYE) SEED EXTRACT | 0.1-5 |
| PALMITOYL TRIPEPTIDE-1 & PALMITOYL TETRAPEPTIDE-7 | 1-5 |
| PLANKTON EXTRACT | 0.1-5 |
| YEAST EXTRACT | 1-3 |
| *PICHIA NAGANISHII* HYDROLYSATE | 0.001-10 |
| *GLYCYRRHIZA GLABRA* EXTRACT | 0.001-5 |
| TRANEXAMIC CETYL ESTER | 0.001-5 |
| ASCORBYL GLUCOSIDE | 0.001-5 |
| WATER | Qs 100 |

These compositions can be applied to the skin every day, in the morning and/or evening.

The invention claimed is:

1. A cosmetic composition comprising, in a physiologically acceptable medium, at least one *Pichia naganishii* hydrolysate, said hydrolysate being obtained by a process comprising at least one step of hydrolysis of *Pichia naganishii*.

2. The cosmetic composition according to claim 1, wherein the hydrolysate is an enzymatic hydrolysate.

3. The cosmetic composition according claim 1, wherein the yeast *Pichia naganishii* is obtained from an exudate of *Camellia japonica*.

4. The cosmetic composition according to claim 1, wherein the hydrolysate comprises between 20% and 60% of proteins by weight of dry matter of the hydrolysate.

5. The cosmetic composition according to claim 1, wherein the hydrolysate is obtained by a process comprising the following steps:
   solubilization of at least 40 g/L of *Pichia naganishii* in water,
   enzymatic hydrolysis,
   separation of soluble and insoluble phase and recovery of the soluble phrases,
   enzymatic inactivation, and
   optionally concentration and sterilizing filtration.

6. The cosmetic composition according to claim 1, wherein the cosmetic composition comprises at least 0.1% by weight of the *Pichia naganishii* hydrolysate.

7. The cosmetic composition according to claim 1, wherein the cosmetic composition is suitable for topical application.

8. A cosmetic method for improving moisturization and/or protecting human skin against drying out and/or improving barrier function, comprising administration of an effective amount of the cosmetic composition according claim 1 to a subject in need thereof.

9. A cosmetic method for reducing skin ageing comprising the administration of an effective amount of the cosmetic composition according to claim 1 to a subject in need thereof.

* * * * *